United States Patent [19]

Petersen et al.

[11] Patent Number: 5,135,533
[45] Date of Patent: * Aug. 4, 1992

[54] COATED GALL-RESISTANT SURGICAL SAW BLADES

[76] Inventors: Thomas D. Petersen, 9680 Alto Dr., La Mesa, Calif. 92041; Kenneth H. Holko, 7384 Trade St., San Diego, Calif. 92121-2422

[*] Notice: The portion of the term of this patent subsequent to Mar. 26, 2008 has been disclaimed.

[21] Appl. No.: 488,554

[22] Filed: Jan. 5, 1990

Related U.S. Application Data

[63] Continuation-in-part of Ser. No. 308,609, Feb. 10, 1989, abandoned.

[51] Int. Cl.$^5$ .............................................. A61B 17/14
[52] U.S. Cl. ...................................... 606/176; 30/351; 30/345; 83/835
[58] Field of Search ................. 606/82, 176, 177, 178, 606/179; 30/345, 351; 63/835

[56] References Cited

U.S. PATENT DOCUMENTS

| | | | |
|---|---|---|---|
| 336,697 | 2/1886 | Clemson | 83/835 |
| 486,426 | 11/1892 | Brooks | 30/348 |
| 563,521 | 7/1896 | Walter | 30/166.3 |
| 1,752,586 | 4/1930 | Bolinder . | |
| 1,929,838 | 10/1933 | Crane | 30/348 X |
| 2,724,417 | 11/1955 | Williams . | |
| 2,730,792 | 1/1956 | Ronan . | |
| 2,958,943 | 11/1960 | Koe | 30/355 X |
| 2,974,051 | 3/1961 | Moore . | |
| 3,496,973 | 2/1970 | Ballard | 30/345 X |
| 3,615,309 | 10/1971 | Dawson . | |
| 3,743,556 | 7/1973 | Breton et al. . | |
| 3,754,968 | 8/1973 | Reznik . | |
| 4,036,236 | 7/1977 | Rhodes, Jr. . | |
| 4,169,637 | 10/1979 | Voitas . | |
| 4,379,121 | 4/1983 | McMurray et al. | 420/452 |
| 4,386,609 | 6/1983 | Mongeon | 606/178 X |
| 4,596,691 | 6/1986 | Ruppert et al. . | |
| 4,671,932 | 6/1987 | Lutz et al. | 420/452 |
| 4,718,413 | 1/1988 | Johnson ., | |

FOREIGN PATENT DOCUMENTS

| | | |
|---|---|---|
| 1503962 | 8/1969 | Fed. Rep. of Germany . |
| 1906532 | 9/1969 | Fed. Rep. of Germany . |
| 1502906 | 2/1970 | Fed. Rep. of Germany . |
| 2021800 | 12/1970 | Fed. Rep. of Germany . |
| 2115358 | 10/1971 | Fed. Rep. of Germany . |
| 150081 | 8/1981 | Fed. Rep. of Germany . |
| 3237655 | 5/1983 | Fed. Rep. of Germany . |
| 2414977 | 8/1979 | France . |

OTHER PUBLICATIONS

U.K. Patent Application 2 179 593 A to Yang.
Japan vol. 13 No. 510.
Japan vol. 6 No. 94.
Japan vol. 7 No. 223.

Primary Examiner—Michael H. Thaler
Attorney, Agent, or Firm—H. Jay Spiegel

[57] ABSTRACT

The present invention relates to a coated gall-resistant surgical saw blades. One such blade includes longitudinal ribs extending outwardly from the opposed faces thereof which combine to define a total blade thickness greater than the width of the lateral extension of the teeth thereof. The ribs are sized and configured to slidably engage a precision slot in a guide means designed to be used to guide the blade in cutting movements. The interaction between the ribs and the slot prevents engagement of the blade teeth with the slot while reducing the surface area of engagement of the blade with the slot to reduce friction. All disclosed blades are coated with a hard, lubricious, metallic, wear resistant coating which is metallurgically bonded to the metallic surface of a respective blade through a coating process forming a part of the present invention.

16 Claims, 2 Drawing Sheets

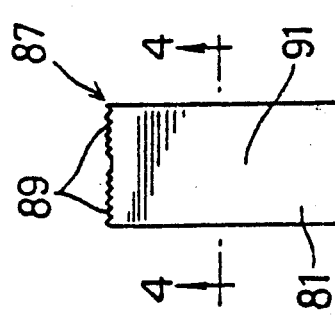
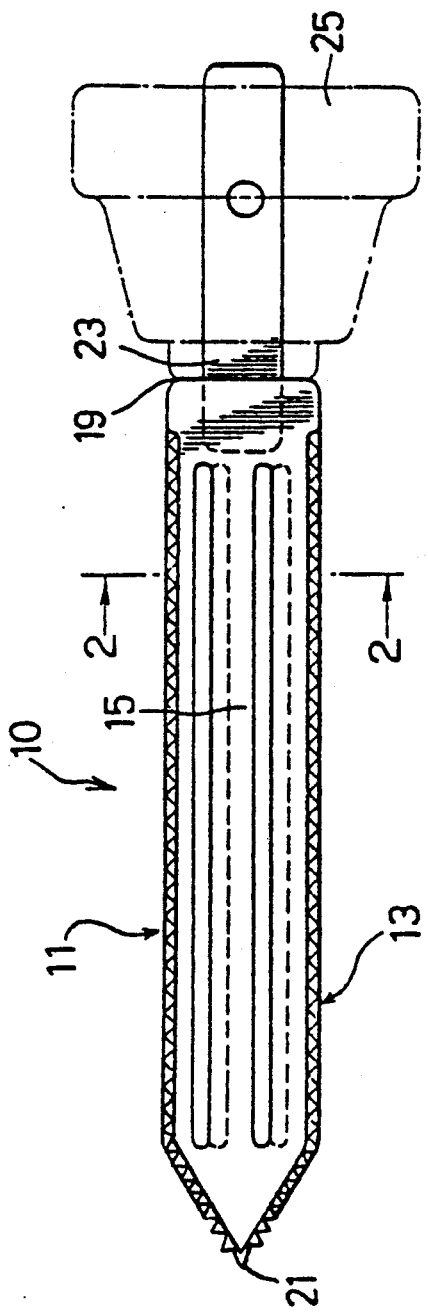
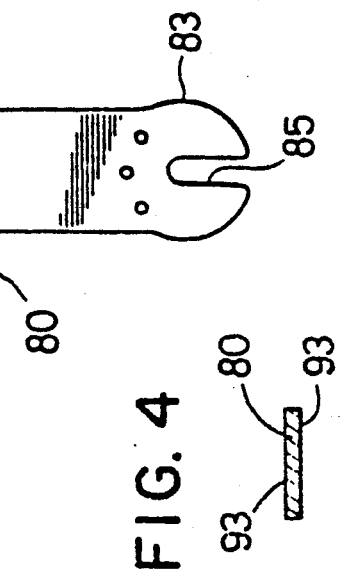
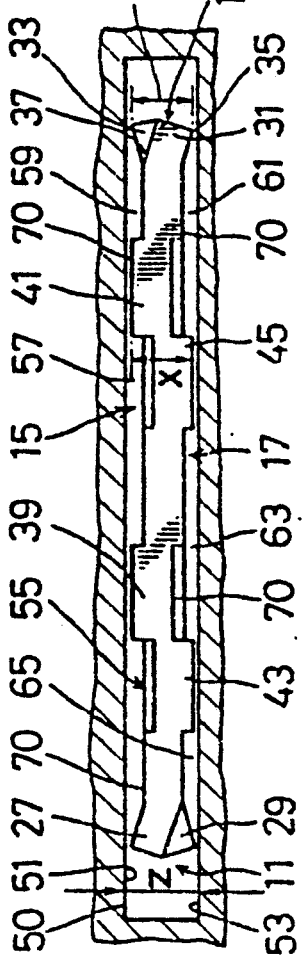

COATED GALL-RESISTANT SURGICAL SAW BLADES

BACKGROUND OF THE INVENTION

The present invention relates to coated gall-resistant surgical saw blades. Orthopedic surgeons utilize saw blades of various shapes and configurations in the performance of surgical procedures. One such saw blade is known as a reciprocating saw blade and is designed to interact with a precision slot which guides the saw blade in reciprocating movements to cut bone tissue during the performance of surgery.

Customarily, a reciprocating surgical blade has a plurality of teeth on each of its two edges. These teeth are customarily provided in a set, that is, consecutive teeth are bent in alternate directions. As this set is provided on known surgical saw blades, the ends of the teeth extend upwardly and downwardly beyond the respective planes of the respective side faces of the blade. Thus, often, it is these ends of the teeth which guide the saw blade within the precision slot. Of course, inherently, this causes wear of the teeth quite prematurely and results in the surgeon having to change saw blades quite often during the surgical case.

Another type of saw blade is known as a sagittal saw blade and consists of a flat elongated blade with a proximal saw engaging slot and a distal transverse surface having a plurality of teeth thereon, with the teeth being flat in configuration, that is, not provided in a set.

These are but two examples of surgical saw blades which may form a part of the present invention.

Studies have been conducted on the effect on bone tissue of blades which have been galled for whatever reason. In an article titled "Orthopedic Saw Blades A Case Study" by H. W. Wevers, et al, published in the journal of Arthroplasty, Volume 2 No.1, March 1987, this problem is discussed. The following is quoted from this article: "Because these blades are used primarily for total knee arthroplasty, it is probable that the damage occurred from direct contact of the cutting edges with metal templates or instruments used in the operation. This type of damage had a direct influence on the mechanical work needed to operate the saw." Later in the publication, the following is stated: "Excessive heat induces thermal damage to osteocytes and expands the zone of necrosis beyond that shown microscopically." Further, the following is stated: "Smooth, accurately cut surfaces are recognized as an important factor for bone ingrowth into porous-coated prostheses. Such clean bone cuts enhance prosthetic fit and setting, therefore promoting an even load bearing to the bone, and improved alignment of the prostheses or osteotomies." Finally, the following is stated: "Damage to blade cutting surfaces due to inadvertent contact with templates and instruments may be unavoidable with currently available techniques."

A publication titled "Avoiding thermal damage to bone: Machining principals applied to powered bone surgery, a literature review", by Ray Umber, et al further discusses the problems attendant in the prior art. The following is disclosed therein: "Thus, cutting with a dull tool, increases the amount of frictional heat generated, much of which is now located in the workpiece itself. With a dull tool not only is the surface of the workpiece increasing in temperature but also the cut is no longer clean."

A further problem with prior art saw blades is also set forth in this publication. In particular, prior art saw blades are so designed that it is difficult to provide water to the site of the operation for cooling purposes and to remove bone chips which are generated during sawing. Due to present saw blade design, "coolant can not reach the dissection site". "It is, therefore, important to allow chip relief and to allow a cooling fluid to reach the dissection site and the dissecting tool. Proper attention to the technique will allow chip relief and the introduction of cooling irrigation, resulting in healthy, living bone which will heal readily."

In a further aspect, applicants have recognized a need to provide a surgical saw blade with a hard coating bonded thereto which will protect the blade surface to thereby increase the lifespan of the blade.

In the past, applicants have attempted to coat a surgical saw blade with polytetraflurorethylene, better known by the trademark TEFLON. Experiments by applicants with TEFLON coated blades have revealed increased efficiency with marked reduction in galling. However, it was found that autoclaving as well as use of the blades in a precision slot would result in the coating stripping off and it was further discovered that chunks of coating would sometimes enter the surgical site. These chunks were very offensive to the surgical site since it was found that the TEFLON flakes were not bio-compatible with the tissues of the patients.

Applicants also experimented with ceramic coatings such as calcium phosphate and aluminum oxide. Experiments with coating surgical saw blades with these materials failed for several reasons. Firstly, the melting point of the ceramics was higher than that of the blade material and, as such, during the coating process, the temper of the blade would be destroyed. Further, it was discovered that a blade coated with ceramic could not be bent or flexed without cracking the coating.

Thereafter, experiments were conducted with combinations of methyl methacrylate and ceramics. While these combinations were superior to the TEFLON, calcium phosphate and aluminum oxide, it was found that adherence to the metallic blades was inferior. Even the milling of grooves to hold the methyl methacrylate and ceramics to the blade did not solve the problems in a satisfactory manner.

As such it was concluded from these experiments that if the blades were to be coated to improve durability thereof and consequently prevent galling, coating with a metallic alloy would have to be employed.

A need has consequently developed for a surgical saw blade which will not only be more durable in use, but which will reduce heat generation adjacent bone tissue while also allowing access of cooling and flushing water to the surgical site.

The following prior art is known to applicant:

| U.S. Pat. No. |
| --- |
| D 30,478 to Earle |
| 864,812 to Thullier |
| 2,670,939 to Harp |
| 3,517,670 to Speelman |
| 4,036,236 to Rhodes, Jr. |

Earle discloses a grass cutting blade having a single rib extending outwardly from one face thereof. Of course, this is different from the teachings of the present invention even concerning the ribbed embodiment thereof in that the present invention contemplates ribs on opposed faces of a blade having teeth formed in a set with the ribs guiding the blade in a precision slot and with the blade coated with a metallic coating.

Thullier discloses a knife and other cutting blade in several embodiments. As the cross-sections demonstrate, each of the blades disclosed in this patent have differing cross-sectional thicknesses at different areas along the lengths thereof which would make it impossible to use these blades in conjunction with a precision slot. Furthermore, none of the embodiments of Thullier teach the use of a metallic coating bonded to the blade.

Harp discloses a mixing paddle having a plurality of rib-like structures thereon which appear to be of differing thicknesses as best seen in FIG. 4. Thus, Harp is quite distinct from the teachings of the present invention as failing to disclose a cutting blade nor a coating therefor and as not being designed for use in conjunction with a precision slot, among other reasons.

Speelman discloses a blood-letting lancet having two longitudinal ribs extending from one face thereof and a point at one or both ends thereof. The present invention is distinct from the teachings of Speelman as including in one embodiment, ribs on opposed faces of an elongated blade having teeth on opposed sides thereof, which teeth are formed in a set configuration and the further provision of a coating bonded thereto.

Finally, Rhodes teaches the concept of a surgical saw blade having teeth on one side thereof and a single elongated longitudinal rib extending outwardly from one face thereof. The lack of a plurality of ribs on opposed faces of the Rhodes, Jr. blade would inherently allow pivoting of the blade from side to side as it moves in a precision slot thus inherently damaging the tooth set.

Concerning the prior art discussed above, as pertains to one embodiment of the present invention, while ribs are disclosed in these patents in conjunction with elongated blades, the ribs are disclosed only for strengthening purposes. While the ribs of one embodiment of the present invention inherently strengthen the elongated blade, their main purpose is to provide guidance of the blade within a precision slot. This is different from the teachings of the prior art.

SUMMARY OF THE INVENTION

The present invention relates to coated gall-resistant surgical saw blades. The present invention includes the following interrelated aspects and features:

a) In a first embodiment, the inventive saw blade consists of an elongated blade having two opposed sides, a distal end, a proximal end and two opposed faces.

b) Each of the opposed sides of the elongated blade has a plurality of teeth formed thereon extending from adjacent the proximal end to adjacent the distal end thereof. In each case, these teeth are formed in a set whereby adjacent teeth are formed or bent in opposed directions whereby the ends of the teeth extend outwardly beyond the respective planes defining the majority of the opposed faces thereof.

c) In this embodiment of the present invention, each of the opposed faces has a plurality of longitudinally extending ribs extending outwardly from each respective face. The ribs extend outwardly from the respective faces of the blade a sufficient distance so that the thickness of the elongated blade from the outward termination of a rib on one face to the outward termination of a rib on the opposed face is greater than the width of the outwardmost extensions of the ends of the respective teeth of the blade as they are formed in the set as defined and described hereinabove. In this way, when the elongated blade is guided in a precision slot, the teeth of the blade will not engage the inner surfaces of the guide slot.

d) The above described precision slot includes a guide slot which is sized and configured to slidably receive an elongated surgical saw blade having the above described ribs formed thereon in a sliding fit in engagement with the ribs only. In this way, the surface area of engagement between the blade and the slot is reduced thereby reducing frictional forces with spaces between the respective ribs allowing water flow through the precision slot with the elongated blade therein thereby enhancing the flushing and cooling effects of the water.

e) A further example of a surgical saw blade which may be coated in accordance with the teachings of the present invention is known as a sagittal saw blade. Such a saw blade consists of a flat elongated blade with a proximal saw engaging slot and a distal transverse surface having a plurality of teeth thereon, with the teeth being flat in configuration, that is, not provided in a set. It should be stressed that the two types of saw blades described hereinabove are but two examples of saw blades which may form a part of the present invention. In fact, the present invention contemplates the coating of any surgical saw blade with the metallic coating described hereinafter and applied through the process described hereinafter.

f) As noted above, the present invention contemplates the coating of a surgical saw blade with a metallic coating. The metallic coating may be described as follows:
  1) The first constituent material which is used in the inventive coating consists of a brazing alloy in a fine powder form, the alloy being made up of, by weight, 14% percent Chromium, 0.1% Silicon, 0.2% Iron, 10% Phosphorus and the balance Nickal. One example of such an alloy is know by the trademark NICROBRAZ 50, a trademark of the Wall Colmonoy Corporation.
  2) The inventive coating material is prepared by mixing the above described brazing alloy with a further brazing alloy in fine powder form which is made up of, by weight, 3.5% Silicon, 1.9% Boron, 1.5% Iron and the balance Nickel. Example of this further brazing alloy are known by the trademarks NICROBRAZ 135 owned by the Wall Colmonoy Corporation and AMDRY 790 owned by Alloy Metals, Inc.
  3) For optimal results, the two above mentioned brazing alloy powders are mixed together in the ratio of 80% of the first mentioned brazing alloy powder and 20% of the second mentioned brazing alloy powder. For optimal results, the powdery nature of the alloys should be to a particle size of −325 mesh or finer.

g) In the method of coating a metallic surgical saw blade with the inventive coating, the surface of the saw blade is first carefully cleaned and is then coated with a binder material. Thereafter, the coating material is dusted onto the surface and adheres thereto due to the presence of the binder. Thereafter, the coating is metallurgically bonded to the metallic surface by heating to the melting temperature of the coating material in a series of heating steps, preferably performed in a vacuum furnace.

Accordingly, it is a first object of the present invention to provide an improved coated gall-resistant surgical saw blade.

It is a further object of the present invention to provide such an improved coated surgical saw blade with a plurality of elongated ribs designed to guide the saw blade in a precision slot while spacing the teeth from engagement with the slot.

It is a yet further object of the present invention to provide such a surgical saw blade whereby the use of ribs enhances the flow of cooling and flushing water to the surgical site.

It is a yet further object of the present invention to provide an improved coated surgical saw blade of the sagittal type having a plurality of flat teeth at the distal end thereof.

It is a yet further object of the present invention to provide a coating material which may be coated onto a surgical saw blade so as to improve the durability thereof.

It is a still further object of the present invention to provide a method of coating the coating material onto a surgical saw blade which results in the coating being metallurgically bonded to the metallic surface of the surgical saw blade which is being coated thereby.

These and other objects, aspects and features of the present invention will be better understood from the following detailed description of the preferred embodiment when read in conjunction with the appended drawing figures.

BRIEF DESCRIPTION OF THE DRAWINGS

FIG. 1 shows a side view of one embodiment of saw blade of the present invention.

FIG. 2 shows a cross-sectional view along the line 2—2 of FIG. 1.

FIG. 3 shows a sideview of a further embodiment of saw blade in accordance with the teachings of the present invention.

FIG. 4 shows a cross-sectional view along the line 4—4 of FIG. 3.

SPECIFIC DESCRIPTION OF THE PREFERRED EMBODIMENTS

Figure 5:
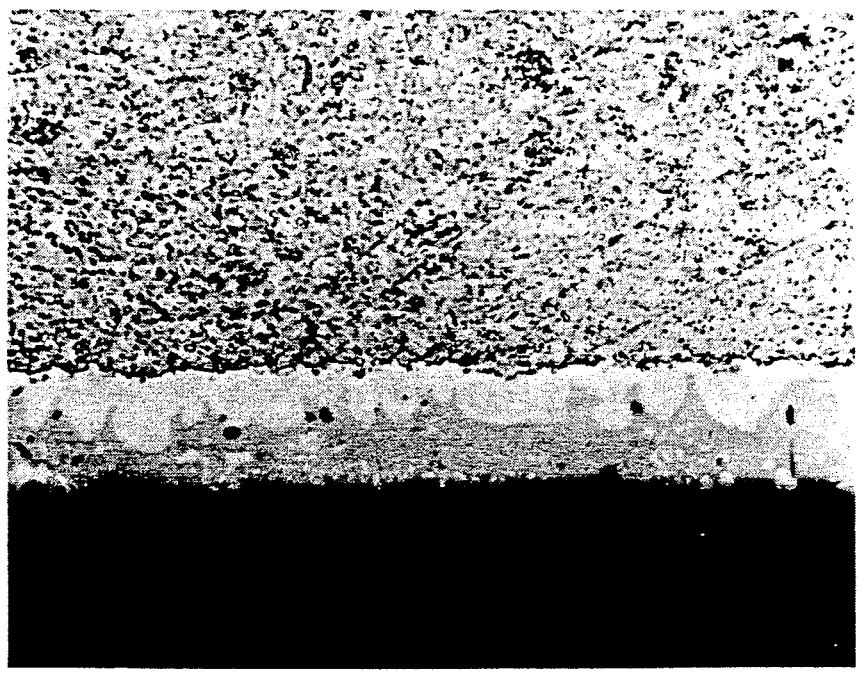
FIG. 5 shows a photomicrograph of a surgical saw blade coated with the coating of the present invention through use of the method disclosed herein, at 500× magnification.

With reference to FIGS. 1 and 2, a first embodiment of inventive blade is generally designated by the reference numeral 10 and is seen to include opposed sides 11 and 13, opposed faces 15 and 17, a proximal end 19 and a distal end 21.

The proximal end 19 has a shank 23 designed to be used to couple the saw blade 10 to the chuck 25 of a reciprocating saw device (not shown). As is well known by those skilled in art, the reciprocating saw device includes a motor whether electrically, hydraulically or pneumatically actuated, which causes controllable reciprocation of the blade 10.

With particular reference to FIG. 2, it is seen that each side 11, 13 of the plate 10 has a plurality of teeth thereon with two teeth being shown on each side of FIG. 2. The two teeth on the side 11 of the blade 10 are designated by the reference numerals 27 and 29 whereas the two teeth on the side 13 are designated by the reference numerals 31 and 33. As is seen in FIG. 2, the respective adjacent teeth are formed in a set whereby, for example, the tooth 27 is bent upwardly and the tooth 29 is bent downwardly. Similarly, the tooth 31 is bent downwardly whereas the tooth 33 is bent upwardly.

In considering the teeth 31 and 33, for example, the tooth 31 has an outwardmost point 35 while the tooth 33 has an outwardmost point 37.

As best seen in FIG. 2, each face 15, 17 of the blade 10 has a plurality of ribs extending outwardly therefrom. Thus, the face 15 has ribs 39 and 41 extending outwardly therefrom whereas the face 17 has ribs 43 and 45 extending outwardly therefrom.

In an important aspect of this embodiment, the thickness of the blade 10 as defined between the outermost extension of the ribs 39 and 43 on the one hand and the ribs 41 and 45 on the other hand is specifically designed to be slightly greater than the thickness of the blade 10 as defined by the distance from the point 35 of the tooth 31 and the point 37 of the tooth 33 as well as the corresponding points on the teeth 27 and 29. FIG. 2 shows a schematic representation of the configuration of a slot 50 termed a precision slot, through which the blade 10 may be guided. The above described relationship between the thickness of the blade 10 at the ribs and the thickness of the blade at the teeth may be best understood by viewing the fact that as the blade 10 is guided within the precision slot 50, the outward faces of the ribs 39, 41, 43, and 45 slidingly engage the inner faces 51, 53 at the slot 50 while the teeth of the blade 10 never engage the faces 51 and 53 of the precision slot 50. Thus, it should be understood that when the blade 10 is guided within the precision slot 50, the elimination of engagement of the teeth with the inner surfaces thereof prevents premature galling of the teeth which would occur through such engagement.

In a further aspect, it should be understood from FIG. 2 that the inclusion of the ribs 39, 41, 43 and 45 on the blade 10 causes the defining of a plurality of passages 55, 57, 59, 61, 63 and 65 between the outer faces of the blade 10 and the inner walls 51 and 53 of the precision slot. These passages allow water to flow through the precision slot 50 while the blade 10 is inserted therein and guided thereby to allow cooling and flushing of the surgical site during sawing operations. This is a distinct advantage over the prior art.

The ribs 39, 41, 43 and 45 may be formed by any suitable means. For example, the blade may be initially manufactured as a flat blade and the ribs may be formed thereon through a stamping operation. Alternatively, the blade may be cast with the blades formed as a part of the casting.

Furthermore, the blade itself may be made of any suitable metallic material. One material which has been found to be effective for use in a surgical saw blade is known in the art as 410 stainless steel.

As seen in FIG. 2, the distance between the outer surfaces of the ribs 39 and 43 is designated by the reference letter x whereas the distance between the point 35 and 37 of the respective teeth 31 and 33 is designated by the reference letter y. In the preferred embodiment of the present invention, the precision slot has a thickness z from face 51 to face 53 of 0.040 inches with dimension x preferably being 0.038 inches and dimension y preferably being 0.036 inches. Thus, in this preferred configuration, which is to be considered merely exemplary, the points 33 and 35 of the teeth 31 and 33 are respectively spaced from the faces 53 and 51 of the precision slot 50 by 0.01 inches each.

As best seen in FIG. 2, a metallic coating 70 is metallurgically bonded to the outer surfaces of the blade 11. The thickness of this coating is included in dimensions X and Y. This metallic coating will be described in greater detail hereinafter.

Now, with reference to FIGS. 3 and 4, a further example of a surgical saw blade which may be coated in accordance with the teachings of the present invention is shown.

FIG. 3 shows a sagittal saw blade 80 which includes an elongated body 81 having a proximal end 83 having a slot 85 designed to allow the mounting of the blade 80 on a suitable saw mechanism. Further, the blade 80 has a distal end 87 having a transverse surface with a plurality of teeth 89 thereon with these teeth being symmetrically formed about a central axis 91 of the blade 80. In the view of FIG. 3, the left-hand teeth point in the left-hand direction whereas the right-hand teeth point in the right-hand direction.

With reference to FIG. 4, it is seen that the blade 80 is coated with a thin coating 93 on both sides thereof. This coating extends throughout the length of the blade 80 including on the sides of the teeth 89 thereof. Again, the particular nature of the this coating and the method of applying the coating on the blade will be described in greater detail hereinafter.

As noted hereinabove, the coating material is made up of two brazing alloys, provided in a powder form of extremely fine particle size of $-325$ mesh or finer. Constituent A, better known as NICROBRAZ 50, consists of, by weight, 14% Chromium, 0.1% Silicon, 0.2% Iron, 10% Phosphorous and the balance Nickel. Constituent B, better known as either NICROBRAZ 135 or AMDRY 790, consists of, by weight, 3.5% Silicon, 1.9% Boron, 1.5 Iron and the balance Nickel.

In the preferred embodiment, the coating material is formed by mixing together 80% by weight of constituent A and 20% by weight of constituent B. While this is the optimal ratio of constituents A and B which are mixed together to form the coating material of the present invention, in fact, one may use between 55% and 90%, by weight, of constituent A and, correspondingly, 10% to 45% by weight of constituent B.

The use of constituent A as a part of the coating material for iron based metallic surfaces is highly unusual due to the resulting formation of hard, brittle compounds. Constituent A is used as a portion of the coating material to provide excellent wear resistance.

With the preferred embodiment of the coating material having been described, the method of coating a metallic surface such as a surgical saw blade using the coating material will now be described in detail. The preferred steps are the following:

1) First, the metallic surface of the saw blade to be coated must first be carefully cleaned to remove all dirt, grease, oil, mill scale, oxides, paint and any other residue from prior processing or other sources. In the example wherein the surface to be coated consists of a surface of precipitation hardened stainless steel or 300 or 400 series stainless steel the cleaning procedure consists of first solvent cleaning the surface to be coated with acetone and thereafter immersing the surface in an acid bath at room temperature for approximately two minutes. In the preferred method, the acid bath which is employed includes, by volume, 12.5 to 25% $HNO_3$, 2.5 to 5% HF and the balance $H_2O$. Immersing in the acid bath allows the acid to etch the surface of the material to be coated while the acid also removes a small amount of material, usually less than one thousandth of an inch, which material includes any surface contaminants.

2) After the surface to be coated has been cleaned, the surface is thereafter coated with a binder material which will remain sticky or which will not dry out for at least several hours. Furthermore, the binder material must be a material which does not contaminate the coating material which is applied thereover later in the processing. One example of a binder material which may be used in accordance with the teachings of the inventive method consists of a binder composition including 75% by volume acetone and 25% by volume Cereclor 42. The binder material may be applied over the surface to be coated either by brushing on the binder material by spraying the binder material in solution form with compressed air through a nozzle or by dipping the surface to be coated in a container of binder.

3) Thereafter, the coating material described hereinabove may be dusted onto the surface of the blade to be coated over the binder material and the coating material will adhere to the surface due to the presence of the binder. As stated hereinabove, for optimal results, the coating material is provided in the form of an extremely fine powder having a particle size of no more than $-325$ mesh.

4) Thereafter, the coating is metallurgically bonded to the metallic surface in a vacuum furnace with the blade being supported by non-metallic supports such as, for example, ceramic supports. Effective results have been obtained when the vacuum furnace is operated at a vacuum level of $10^{-4}$ torr. The following is the preferred furnace cycle which should be used in obtaining optimal metallurgical bonding of the coating material on the blade:

STEP 1: Heat to 700-800 degrees F. and hold for 15-25 minutes to drive binder off.

STEP 2: Heat to 1500-1550 degrees F. and hold for 15-25 minutes to stabilize temperatures in the furnace.

STEP 3: Heat rapidly to from 1650-1670 degrees F. and hold for between 5 and 10 minutes to accomplish melting and bonding of the coating material on the metallic surface of the blade. When the ratio of Constituent A and Constituent B is at the preferred ratio of 80% to 20%, this step may be carried out at temperatures of up to 1850 degrees F. for a time period of up to 15 minutes.

STEP 4: Cool the furnace. One way of cooling the furnace is by back filling with inert gas. For hardenable alloys, an internal fan may be used to rapidly cool coated components and develop base metal strength. For non-hardenable alloys, furnace cooling is acceptable.

For optimal results, the blade which is to be coated must be supported within the furnace in a flat position to avoid running and uneven buildup of the coating material. As stated above, the blade must be supported in a manner preventing touching of other metallic surfaces to avoid joining. This may be accomplished, again, through the use of ceramic supports with the ceramic being made from $AL_2O_3$ or combinations of $AL_2O_3$ and $SiO_2$.

Use of a vacuum furnace is made to avoid oxidation of the coating and substrate. Alternatively, the heating may be accomplished in a high purity inert gas atmosphere or a high purity reducing atmosphere such as one including hydrogen.

As should be understood, during melting of the coating and alloying with the component surface, intermetallic compounds such as silicides, borides, phosphides and carbides are formed in the coating. These compounds are extremely hard and lubricious and give the coating its high hardness and wear resistance.

Coatings have been carried out in accordance with the above described method of coating. Coating hardness of up to Rc59 has been measured with coating thicknesses of one to two thousandths of a inch being measured. The hardness of Rc59 is obtained through conversion from DPH microhardness. The photomicrograph comprising FIG. 5 shows high quality metallurgical bonding of the coating to the metallic saw blade on which it has been coated. As shown in FIG. 5, the coating is quite uniform, has high quality, and adherence is excellent. FIG. 5 illustrates the coating as formed on a surgical saw blade made of 410 stainless steel.

Wear tests on saw blades such as those illustrated in FIGS. 1–4, which have been coated in accordance with the teachings of the present invention show that the coating is quit capable of protecting the side faces of the blade against galling while protecting the blade teeth and increasing their life span. The coating has shown no significant wear after experiencing sliding engagement with a stainless steel precision slot guide device. Due to the reduced wear and friction, heating of the surgical blade is significantly reduced which results in less thermal damage to the bone which is being cut thereby.

In a further aspect, a surgical blade such as that which is shown in FIG. 5 as coated in accordance with the teachings of the present invention was bent through 90 degrees around a one quarter inch diameter mandrill without any cracking of the coating taking place. This is considered to be excellent ductility for a coating of this type.

In coating a surgical saw blade, the amount of coating must be carefully controlled so that the teeth are not filled with coating and so that the blade thickness is not excessively increased. Additionally, the blade must be supported during firing in the vacuum furnace so that excessive coating buildup does not occur. This requires that a portion of the coated surface may come in contact with support means for the blade during melting and bonding. Accordingly, the support means should comprise a thin aluminum oxide tool which will not bond to the coating.

Accordingly, an invention has been disclosed in terms of a preferred embodiment which fulfills each and every one of the objects of the invention set forth hereinabove and provides embodiments of coated saw blades of increased strength and life and which reduce bone tissue damage in use.

Of course, various changes, modifications and alterations in the teachings of the present invention may be contemplated by those skilled in the art without departing from the intended spirit and scope of the present invention. As such, it is intended that the present invention only be limited by the terms of the appended claims.

We claim:

1. A surgical saw blade for use in conjunction with a precision slot having parallel guiding faces, comprising:

a) an elongated body having first and second faces lying in substantially parallel planes and extending substantially the entire length of said elongated body, one of said first and second faces having at least one longitudinal rib protruding outwardly therefrom, the other of said first and second faces having at least two longitudinal ribs protruding outwardly therefrom and laterally staggered with respect to said at least one longitudinal rib;

b) said blade having two sides defining the lateral extent of said first and second faces, at least one of said sides having a plurality of teeth thereon, respective adjacent pairs of said teeth defining a first thickness in a direction perpendicular to said substantially parallel planes;

c) said first thickness being less than a second thickness defined by the outward extent of opposed said ribs whereby when said blade is inserted in a slot, said parallel guiding faces solely engage said ribs and said teeth are maintained spaced therefrom;

d) said first and second faces being coated with a hard, metallic, wear resistant coating.

2. The invention of claim 1, wherein said one of said first and second faces has at least two said ribs extending outwardly therefrom.

3. The invention of claim 1, wherein said teeth are formed in a set.

4. The invention of claim 3, wherein each of said sides has a plurality of teeth thereon.

5. The invention of claim 1, wherein said ribs have flat terminating faces, said ribs being formed by stamping said blade.

6. The invention of claim 1, wherein said ribs have flat terminating faces and said blade is cast with said ribs formed during casting.

7. The invention of claim 1, wherein said blade is made of stainless steel.

8. The blade of claim 1, wherein said coating further comprises a nickel based alloy, said alloy including, by weight, at least 75% nickel.

9. The blade of claim 8, wherein said nickel based alloy comprises first and second alloys mixed together and coated on said blade.

10. The blade of claim 9, wherein said first alloy includes, by weight, approximately 14% Chromium, 0.1% Silicon, 0.2% Iron, 10% Phosphorus and the balance Nickel.

11. The blade of claim 10, wherein said second alloy includes, by weight, approximately 3.5% Silicon, 1.5% Iron, 1.9% Boron and the balance Nickel.

12. The blade of claim 11, wherein said nickel based alloy includes 55–90% of said first alloy and 10–45% of said second alloy.

13. The blade of claim 12, wherein said nickel based alloy includes 80% of said first alloy and 20% of said second alloy.

14. The blade of claim 1, wherein said body includes a proximal end with a tool engaging shank and a distal end.

15. The blade of claim 14, wherein said teeth are formed on at least one of said side edges.

16. The blade of claim 1, wherein said teeth are formed on both of said sides.

* * * * *